(12) United States Patent
Berkman et al.

(10) Patent No.: US 10,195,347 B1
(45) Date of Patent: Feb. 5, 2019

(54) AUTO-ILLUMINATING SYRINGE

(71) Applicants: Jacquelyn Berkman, Hauppauge, NY (US); Jessica Berkman, Hauppauge, NY (US)

(72) Inventors: Jacquelyn Berkman, Hauppauge, NY (US); Jessica Berkman, Hauppauge, NY (US)

(*) Notice: Subject to any disclaimer, the term of this patent is extended or adjusted under 35 U.S.C. 154(b) by 0 days.

(21) Appl. No.: 15/620,914

(22) Filed: Jun. 13, 2017

(51) Int. Cl.
*A61M 5/31* (2006.01)

(52) U.S. Cl.
CPC ............ *A61M 5/31* (2013.01); *A61M 5/3129* (2013.01); *A61M 2005/3125* (2013.01); *A61M 2205/587* (2013.01)

(58) Field of Classification Search
CPC . A61M 5/31; A61M 5/3129; A61M 2205/587
See application file for complete search history.

(56) References Cited

U.S. PATENT DOCUMENTS

| | | | |
|---|---|---|---|
| 5,062,828 | A | 11/1991 | Waltz |
| 5,254,101 | A | 10/1993 | Trombley, III |
| 5,900,291 | A | 5/1999 | Pebbles |
| 6,764,469 | B2 | 7/2004 | Broselow |
| D661,389 | S | 6/2012 | Morgan |
| 2005/0080384 | A1* | 4/2005 | Green, Jr. .......... A61M 5/31511 604/218 |
| 2006/0084925 | A1 | 4/2006 | Ramsahoye |
| 2010/0145274 | A1 | 6/2010 | Royce |
| 2011/0196312 | A1* | 8/2011 | DeVega ................ A61M 5/427 604/218 |
| 2015/0346513 | A1 | 12/2015 | Heacock |
| 2016/0151575 | A1 | 6/2016 | Foster |

FOREIGN PATENT DOCUMENTS

WO        2015184093        12/2015

* cited by examiner

*Primary Examiner* — Edelmira Bosques
(74) *Attorney, Agent, or Firm* — Kyle A. Fletcher, Esq.

(57) ABSTRACT

The auto-illuminating syringe is configured for use with a syringe. The auto-illuminating syringe is configured for use in delivering an electrolytic media. Wherein the electrolytic media is delivered into a body through the syringe. The auto-illuminating syringe increases the contrast between the electrolytic media and the background such that the electrolytic media may be more readily seen when a dose is being drawn into the syringe. The auto-illuminating syringe comprises a plunger and an illumination circuit. The illumination circuit is contained within the plunger. The plunger is configured for use in pumping fluids out of the syringe. The illumination circuit generates a distinctive light that illuminates the electrolytic media in manner that allows the electrolytic media to be readily seen. The illumination circuit is activated by the presence of the electrolytic media.

18 Claims, 4 Drawing Sheets

AUTO-ILLUMINATING SYRINGE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science, more specifically, an illuminated device for introducing media into a body.

SUMMARY OF INVENTION

The auto-illuminating syringe is configured for use with a syringe. The auto-illuminating syringe is configured for use in delivering an electrolytic media. Wherein the electrolytic media is delivered into a body through the syringe. The auto-illuminating syringe increases the contrast between the electrolytic media and the background such that the electrolytic media may be more readily seen when a dose is being drawn into the syringe. The auto-illuminating syringe comprises a plunger and an illumination circuit. The illumination circuit is contained within the plunger. The plunger is configured for use in pumping fluids out of the syringe. The illumination circuit generates a distinctive light that illuminates the electrolytic media in manner that allows the electrolytic media to be readily seen. The illumination circuit is activated by the presence of the electrolytic media.

These together with additional objects, features and advantages of the auto-illuminating syringe will be readily apparent to those of ordinary skill in the art upon reading the following detailed description of the presently preferred, but nonetheless illustrative, embodiments when taken in conjunction with the accompanying drawings.

In this respect, before explaining the current embodiments of the auto-illuminating syringe in detail, it is to be understood that the auto-illuminating syringe is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the auto-illuminating syringe.

It is therefore important that the claims be regarded as including such equivalent construction insofar as they do not depart from the spirit and scope of the auto-illuminating syringe. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
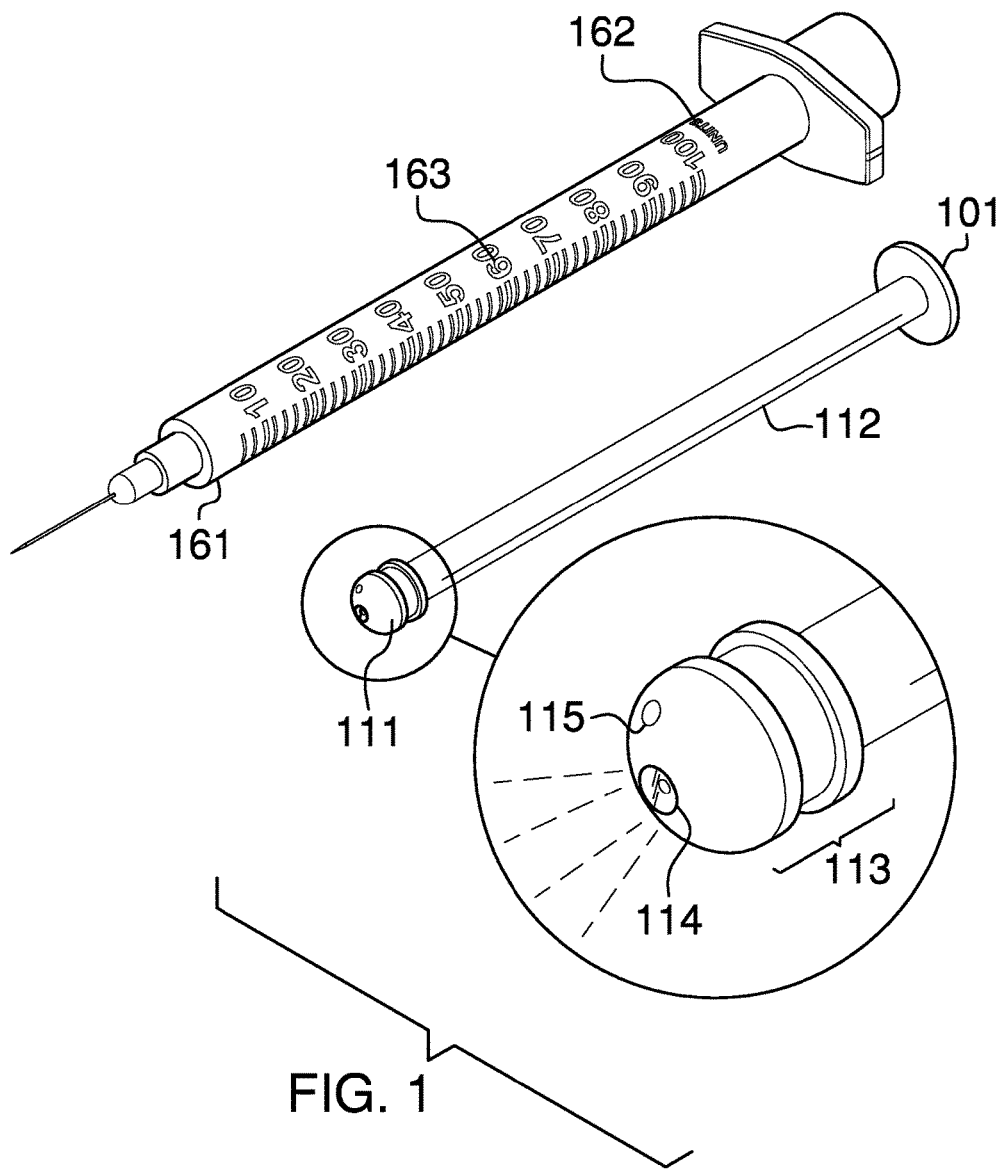
FIG. 1 is a perspective view of an embodiment of the disclosure.
Figure 2:
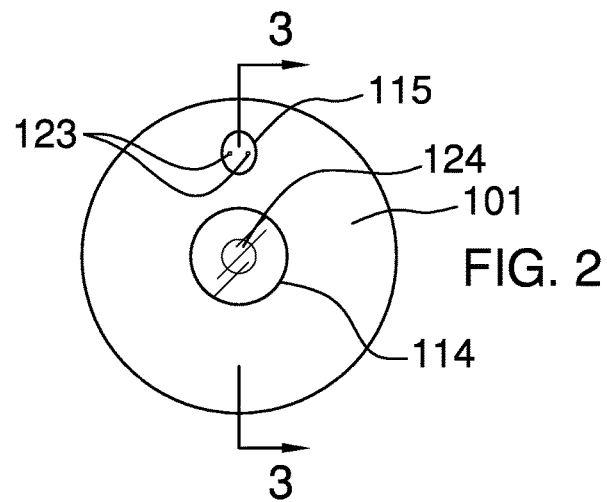
FIG. 2 is a front view of an embodiment of the disclosure.
Figure 3:
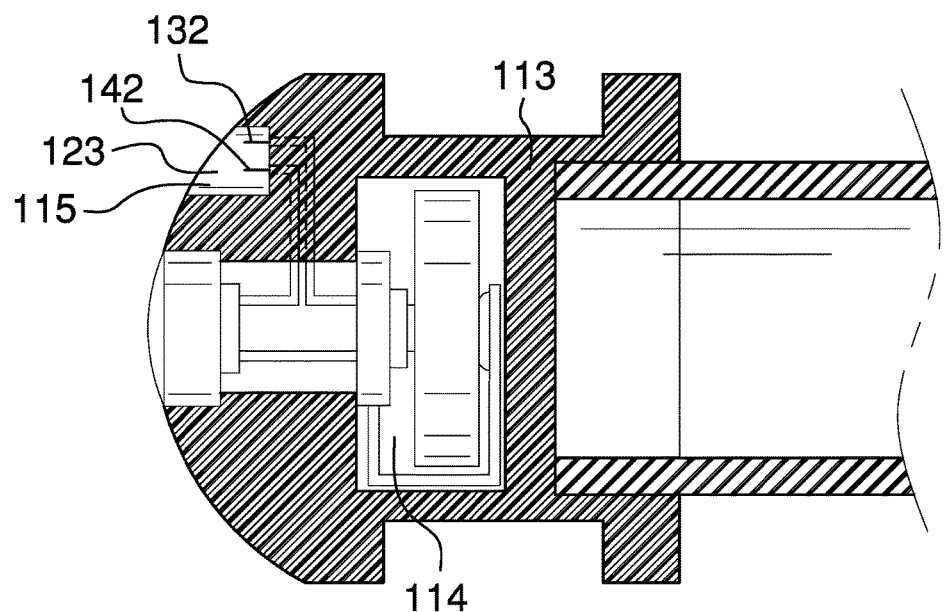
FIG. 3 is a cross-sectional view of an embodiment of the disclosure across 3-3 as shown in FIG. 2.
Figure 4:
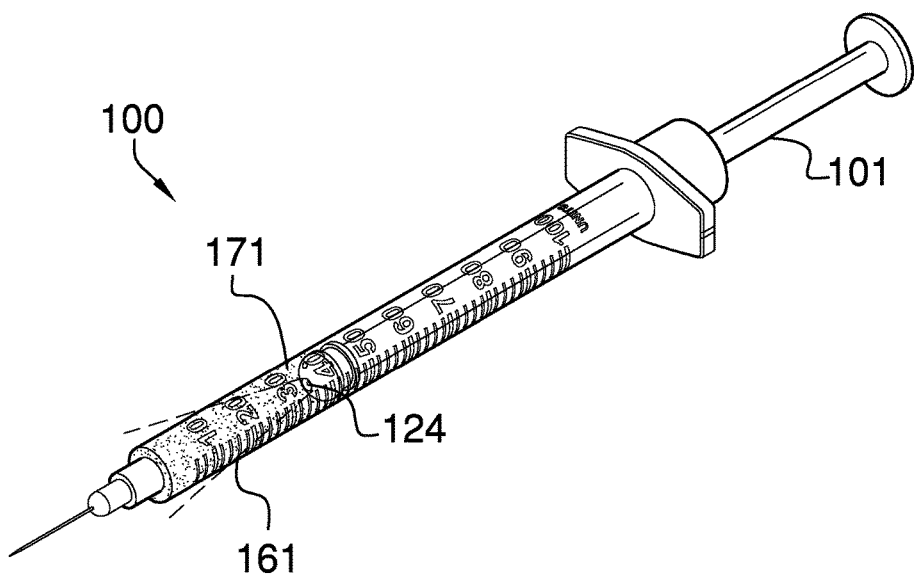
FIG. 4 is an in use view of an embodiment of the disclosure.
Figure 5:
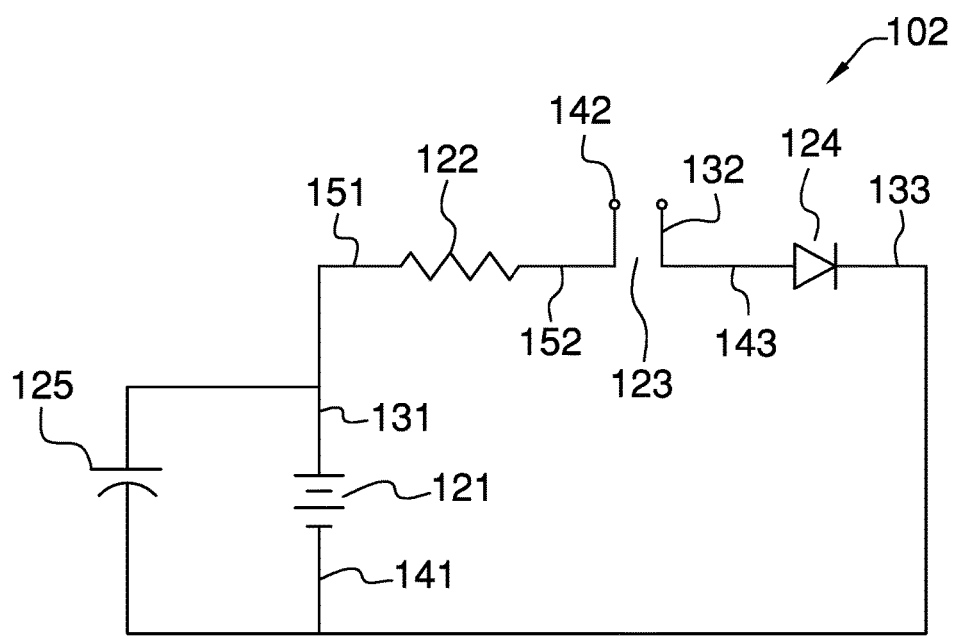
FIG. 5 is a block diagram or schematic view of an embodiment of the disclosure.

Detailed reference will now be made to one or more potential embodiments of the disclosure, which are illustrated in FIGS. 1 through 5.

The auto-illuminating syringe 100 (hereinafter invention) is configured for use with a syringe 161. The invention 100 is configured for use in delivering an electrolytic media 171. Wherein the electrolytic media 171 is delivered into a body through the syringe 161. The syringe 161 is further defined with a barrel 162 and scale markings 163. The barrel 162 contains the electrolytic media 171. The scale markings 163 is a graduated scale that measures partial volumes within the syringe 161. The scale markings 163 are used for drawing a proper dose of the electrolytic media 171. The invention 100 increases the contrast between the electrolytic media 171 and the background such that the electrolytic media 171 may be more readily seen against the scale markings 163 when a dose is being drawn into the syringe 161. The invention 100 comprises a plunger 101 and an illumination circuit 102. The illumination circuit 102 is contained within the plunger 101. The plunger 101 is configured for use in pumping fluids into and out of the syringe 161. The illumination circuit 102 generates a distinctive light that illuminates the electrolytic media 171 in manner that allows the electrolytic media 171 to be readily seen. The illumination circuit 102 is activated by the presence of the electrolytic media 171.

The syringe 161 is a device that is used to measure, transport, and deliver a fluid. The barrel 162 refers to a hollow cylindrical structure that contains the fluid being measured by the syringe 161. The barrel 162 is formed from a transparent material. The scale markings 163 refers to graduated markings on the barrel 162 that are used to measure the volume of fluid within the syringe 161.

The electrolytic media 171 refers to a therapeutic electrolytic solution. In the first potential embodiment of the disclosure, the electrolytic media 171 comprises a pharmacologically active media dissolved in a PBS solution.

The plunger 101 is a piston that is inserted into the barrel 162 of the syringe 161. The plunger 101 forms a fluid impermeable seal with the interior wall of the barrel 162. The plunger 101 is used to draw the electrolytic media 171 into the barrel 162 during dosing and is used to eject the electrolytic media 171 from the barrel 162 of the electrolytic media 171. The plunger 101 comprises a tip 111 and a shaft 112.

The shaft 112 is a rigid linear structure that forms a handle that allows for the manipulation of the tip 111 when the tip 111 is inserted into the barrel 162.

The tip 111 is formed at the end of the shaft 112 that is inserted into the barrel 162 of the syringe 161. The tip 111 forms the fluid impermeable seal within the barrel 162. When the plunger 101 is withdrawn from the barrel 162 a vacuum is created that draws the electrolytic media 171 into the barrel 162. When the plunger 101 is pressed into the barrel 162, the tip 111 of the plunger 101 ejects the electrolytic media 171.

The tip 111 comprises an elastomeric structure 113 that is further formed with a primary cavity 114 and a switch cavity 115.

In the first potential embodiment of the disclosure, the tip 111 is a roughly disk shaped structure that is mounted on the shaft 112 such that the center axis of the tip 111 is aligned with the center axis of the shaft 112. The tip 111 is further defined with an outer diameter. The barrel 162 is further defined with an inner diameter. The tip 111 is an elastomeric structure 113 formed from an elastomeric material. The elastomeric structure 113 of the tip 111 is formed such that the outer diameter of the tip 111 is greater than the inner diameter of the barrel 162. This size differential requires that the elastomeric structure 113 be compressed when the tip 111 is inserted into the barrel 162. The force generated by the elastomeric structure 113 against the interior wall of the barrel 162 as the elastomeric structure 113 attempts to return to its relaxed shape forms the seal between the tip 111 and the interior surface of the barrel 162.

The primary cavity 114 is an aperture that is formed into the tip 111. As shown most clearly in FIG. 3, the primary cavity 114 contains all the elements of the illumination circuit 102 with the exception of the electrolytic switch 123. The illumination circuit 102 including the electrolytic switch 123 and the LED 124 are discussed in greater detail elsewhere in this disclosure. The LED 124 of the illumination circuit 102 is installed in the primary cavity 114 such that the light generated by the LED 124 will illuminated the electrolytic media 171. As shown most clearly in FIG. 3, the switch cavity 115 is an aperture that is formed into the tip 111. The electrolytic switch 123 is installed in the switch cavity 115 such that the electrolytic switch 123 is immersed in the electrolytic media 171 when the electrolytic media 171 is drawn into the syringe 161.

The illumination circuit 102 is an electrical circuit that is mounted in the plunger 101. The illumination circuit 102 is configured to illuminate the electrolytic media 171 in a contrasting color for the purpose of illuminating a dose of the electrolytic media 171 and to improve the visibility of the scale markings 163. The illumination circuit 102 comprises a battery 121, a limit resistor 122, an electrolytic switch 123, and an LED 124. The electrolytic switch 123 comprises a second cathode 132 and a second anode 142. The battery 121 is further defined with a first cathode 131 and a first anode 141. The LED 124 is further defined with a third cathode 133 and a third anode 143. The limit resistor 122 is further defined with a first lead 151 and a second lead 152.

The battery 121 is a commercially available chemical device that is used to power the illumination circuit 102. The first cathode 131 is commonly referred to as the positive terminal of the battery 121. The first anode 141 is commonly referred to as the negative terminal of the battery 121.

The LED 124 is a light source that is used to illuminate the electrolytic media 171 and the scale markings 163 of the syringe 161. The third cathode 133 is the lead of the LED 124 that has the lower voltage potential when the LED 124 is illuminated. The third anode 143 is the lead of the LED 124 that has the higher voltage potential when the LED 124 is illuminated.

The electrolytic switch 123 is a switch that is actuated by the electrolytic media 171. When the electrolytic switch 123 is immersed in the electrolytic media 171, the ions contained within the electrolytic media 171 transport the electrons contained within the electric current from the second cathode 132 to the second anode 142 (i.e. the current flows from the second anode 142 to the second cathode 132). The second cathode 132 is an electrode associated with the electrolytic switch 123 that forms a conductive interface with the electrolytic media 171. The second cathode 132 is inserted in the electrolytic media 171. The second anode 142 is an electrode associated with the electrolytic switch 123 that forms a conductive interface with the electrolytic media 171. The second anode 142 is inserted in the electrolytic media 171.

The limit resistor 122 is an electrical device that is used to limit the current flow through the illumination circuit 102, The limit resistor 122: 1) limits the current flow through the LED 124; and, 2) limits current flow through the electrolytic media 171 for the purposes of limiting unwanted or unnecessary chemical reactions within the electrolytic media 171. The first lead 151 is an electrical connection to the limit resistor 122. The second lead 152 is an electrical connection to the limit resistor 122.

To form the first potential embodiment of the disclosure, a series circuit comprising the battery 121, the limit resistor 122, the electrolytic switch 123, and the LED 124 is assembled. The immersion of the electrolytic switch 123 into the electrolytic media 171 closes the electrolytic switch 123 to illuminate the LED 124. By conducting electricity between the second cathode 132 and the second anode 142, the electrolytic switch 123 effectively completes the series circuit.

The first cathode 131 of the battery 121 is electrically connected to the first lead 151 of the limit resistor 122. The second lead 152 of the limit resistor 122 is electrically connected to the second anode 142 of the electrolytic switch 123. The second cathode 132 of the electrolytic switch 123 is electrically connected to the third anode 143 of the LED 124. The third cathode 133 of the LED 124 is electrically connected to the first anode 141 of the battery 121. The LED 124 is selected such that the LED 124 will illuminate the electrolytic media 171 in a contrasting color. It is preferred that the color of the LED 124 be a violet (440 nM to 480 nM) LED 124 for this purpose.

In circumstances where the voltage drop across the electrolytic switch 123 is too great to drive the LED 124, the current flowing through the electrolytic switch 123 may instead be used to trigger a transistor to drive the LED 124.

The use of transistors in this manner is well known and documented in the electrical arts. In a third potential embodiment of the disclosure, the battery 121 may be replaced with a capacitor 125 sized to provide electrical power long enough to draw a dose of the electrolytic media 171. This scenario is primarily intended for smaller syringes 161. The capacitor 125 is need not be used in conjunction with the battery 121.

The following definitions were used in this disclosure:

Anodes and Cathodes: As used in this disclosure, an anode and a cathode are the connecting terminals of an electrical circuit element or device. Technically, the cathode is the terminal through which the physical electrons flow into the device. The anode is the terminal through which the physical electrons flow out of the device. As a practical matter the anode refers to: 1) the positive terminal of a power consuming electrical circuit element; 2) the negative terminal of a discharging battery or an electrical power source; and, 3) the positive terminal of a charging battery. As a further practical matter the cathode refers to: 1) the negative terminal of a power consuming electrical circuit element; 2) the positive terminal of a discharging battery or an electrical power source; and, 3) the negative terminal of a charging battery.

Battery: As used in this disclosure, a battery is a container consisting of one or more cells, in which chemical energy is converted into electricity and used as a source of power.

Buffer: As used in this disclosure, a buffer is a solution that resists changes to pH in response to the addition of acidic or base solutions.

Capacitor: As used in this disclosure, a capacitor is an electrical device that is used to store an electric charge.

Cavity: As used in this disclosure, a cavity is an empty space or negative space that is formed within an object.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or cone like structure. When the center axes of two cylinder or like structures share the same line they are said to be aligned. When the center axes of two cylinder like structures do not share the same line they are said to be offset.

Cylinder: As used in this disclosure, a cylinder is a geometric structure defined by two identical flat and parallel ends, also commonly referred to as bases, which are circular in shape and connected with a single curved surface, referred to in this disclosure as the face. The cross section of the cylinder remains the same from one end to another. The axis of the cylinder is formed by the straight line that connects the center of each of the two identical flat and parallel ends of the cylinder. Unless otherwise stated within this disclosure, the term cylinder specifically means a right cylinder which is defined as a cylinder wherein the curved surface perpendicularly intersects with the two identical flat and parallel ends.

Diameter: As used in this disclosure, a diameter of an object is a straight line segment that passes through the center of an object. The line segment of the diameter is terminated at the perimeter or boundary of the object through which the line segment of the diameter runs.

Diode: As used in this disclosure, a diode is a two terminal semiconductor device that allows current flow in only one direction. The two terminals are called the anode and the cathode. Electric current is allowed to pass from the anode to the cathode.

Disk: As used in this disclosure, a disk is a cylindrically shaped object that is flat in appearance.

Dose: As used in this disclosure, the term dose refers to a specified measured quantity of a chemical substance that is to be incorporated or introduced into an organism or a mixture such as a recipe or a solution. The term dose often, but not necessarily, implies the introduction of a therapeutic substance.

Elastic: As used in this disclosure, an elastic is a material or object that deforms when a force is applied to it and that is able to return to its relaxed shape after the force is removed. A material that exhibits these qualities is also referred to as an elastomeric material.

Electrolyte: As used in this disclosure, an electrolyte refers to ionic atomic or polyatomic compounds that dissolve in water to create an electrically conductive solution referred to as an electrolytic solution.

Electrolysis: As used in this disclosure, electrolysis refers to an oxidation reduction chemical reaction created by passing an electric current through an electrolytic solution.

Inner Diameter: As used in this disclosure, the term inner diameter is used in the same way that a plumber would refer to the inner diameter of a pipe.

Ion: As used in this disclosure, an ion is an atom or a molecule with a net electric charge.

Ionic Bond: As used within this disclosure, an ionic bond refers to a chemical bond between a first atom and a second atom wherein the first atom takes an electron from the second atom. This is in contrast to a covalent bond.

Lead: As used in this disclosure, a lead is a conductor that is physically used to electrically connect an electrical component into a larger circuit assembly.

LED: As used in this disclosure, an LED is an acronym for a light emitting diode. A light emitting diode is a diode that is also a light source.

Limit Resistor: As used in this disclosure, a limit resistor is an electrical resistor that is used to limit the flow of electric current through an electrical circuit.

Molarity: As used in this disclosure, molarity is a measure of concentration that measures the moles of a solute in a liter of solution.

Osmolarity: As used in this disclosure, osmolarity refers to the molarity of the totals particles (other than the solvent) dissolved in a solution. Osmolarity is used for osmotic pressure calculations.

Osmosis: As used in this disclosure, osmosis refers to the flow of a solute across a semi-permeable membrane in response to a concentration gradient that exists across the semi-permeable membrane.

Outer Diameter: As used in this disclosure, the term outer diameter is used in the same way that a plumber would refer to the outer diameter of a pipe.

PBS Solution: As used in this disclosure, a PBS solution refers to a phosphate buffer saline solution. A phosphate buffered saline solution is a solution containing sodium phosphate and sodium chloride dissolved in water. Optionally, a buffer may also contain potassium chloride or potassium phosphate. A PBS solution is a well-known solution that is intended to match the osmolarity and ionic concentration found in most animals including humans for the purpose of avoiding unwanted osmotic reactions. PBS solutions are often used to store and deliver medications. PBS solutions are commonly referred to, and within this disclosure are considered to be equivalent to, a PBS buffer.

Pharmacologically Active Media: As used in this disclosure, a pharmacologically active media refers to a chemical substance that has a biochemical or physiological effect on a biological organism.

Plunger: As used in this disclosure, a plunger is a cylindrical piston that is used to pump fluids out of a syringe.

Relaxed Shape: As used in this disclosure, a structure is considered to be in its relaxed state when no shear, strain, or torsional forces are being applied to the structure.

Scale: As used in this disclosure, refers to a visual system of ordered markings that are used as a reference for measurement.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Syringe: As used in this disclosure, a syringe is a device that is used to measure fluids. In a medical setting, a syringe is used to inject fluids into a body or draw fluids from a body in a measurable manner. A syringe generally comprises a hollow cylindrical barrel and a plunger.

Transistor: As used in this disclosure, a transistor is a general term for a three terminal semiconducting electrical that is used for electrical signal amplification and electrical switching applications. There are several designs of transistors. A common example of a transistor is an NPN transistor that further comprises a collector terminal, an emitter terminal, and a base terminal and which consists of a combination of two rectifying junctions (a diode is an example of a rectifying junction). Current flowing from the collector terminal through the emitter terminal crosses the two rectifier junctions. The amount of the electric current crossing the two rectified junctions is controlled by the amount of electric current that flows through the base terminal. The transistor operates as switch. When a voltage is applied to the base, current will flow into the base and the transistor will act like a closed switch allowing current to flow from the collector to the emitter. When the voltage is removed from the base, the transistor will act like an open switch disrupting current flow from the collector to the emitter.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A medical device comprising:
a plunger and an illumination circuit;
wherein the illumination circuit is contained within the plunger;
wherein the medical device is configured for use with a syringe;
wherein the medical device is configured for use in delivering an electrolytic media;
wherein the electrolytic media is delivered through the syringe;
wherein the syringe is further defined with a barrel and scale markings;
wherein the barrel is transparent;
wherein the medical device provides a visual contrast between the electrolytic media and a background;
wherein the electrolytic media refers to a pharmacologically active media dissolved in an electrolytic solution;
wherein the plunger is configured for use in pumping fluids into and out of the barrel;
wherein the illumination circuit generates a light that illuminates the electrolytic media;
wherein the illumination circuit is activated by the presence of the electrolytic media.

2. The medical device according to claim 1
wherein the plunger is a piston that is inserted into the barrel of the syringe;
wherein the plunger forms a fluid impermeable seal with the interior wall of the barrel.

3. The medical device according to claim 2
wherein the plunger comprises a tip and a shaft;
wherein the shaft is a rigid linear structure;
wherein the tip is formed at the end of the shaft that is inserted into the barrel of the syringe;
wherein the tip is mounted on the shaft such that the center axis of the tip is aligned with the center axis of the shaft.

4. The medical device according to claim 3 wherein the tip forms the fluid impermeable seal within the barrel.

5. The medical device according to claim 4
wherein the tip comprises an elastomeric structure that is further formed with a primary cavity and a switch cavity;
wherein the tip is further defined with an outer diameter;
wherein the barrel is further defined with an inner diameter.

6. The medical device according to claim 5
wherein the elastomeric structure is formed from an elastomeric material;
wherein the elastomeric structure of the tip is formed such that the outer diameter of the tip is greater than the inner diameter of the barrel;
wherein the elastomeric is compressed when the tip is inserted into the barrel;
wherein the force generated by the elastomeric structure against the interior wall of the barrel as the elastomeric structure attempts to return to its relaxed shape forms the seal between the tip and the interior surface of the barrel.

7. The medical device according to claim 6
wherein the primary cavity is an aperture that is formed into the tip;
wherein the switch cavity is an aperture that is formed into the tip.

8. The medical device according to claim 7
wherein the illumination circuit is an electrical circuit;
wherein the illumination circuit comprises a battery, a limit resistor, an electrolytic switch, and an LED;
wherein the battery, the limit resistor, the electrolytic switch, and the LED are electrically interconnected;
wherein the electrolytic switch comprises a second cathode and a second anode;
wherein the battery is further defined with a first cathode and a first anode;
wherein the LED is further defined with a third cathode and a third anode;
wherein the limit resistor is further defined with a first lead and a second lead.

9. The medical device according to claim 8
wherein the battery is a chemical device that powers the illumination circuit;
wherein the LED is a light source;
wherein the electrolytic switch is a switch that is actuated by the electrolytic media;
wherein the immersion of the electrolytic switch into the electrolytic media closes the electrolytic switch;
wherein the limit resistor is an electrical device that limits the current flow through the illumination circuit.

10. The medical device according to claim 9
wherein the first cathode of the battery is electrically connected to the first lead of the limit resistor;
wherein the second lead of the limit resistor is electrically connected to the second anode of the electrolytic switch;
wherein the second cathode of the electrolytic switch is electrically connected to the third anode of the LED;
wherein the third cathode of the LED is electrically connected to the first anode of the battery;
wherein the LED is selected such that the LED will illuminate the electrolytic media in a contrasting color;
wherein it is preferred that the color of the LED be a violet (440 nm to 480 nm) LED for this purpose.

11. The medical device according to claim 10 wherein the illumination circuit further comprises a transistor.

12. The medical device according to claim 11 wherein the electrolytic media comprises a pharmacologically active media dissolved in a PBS solution.

13. The medical device according to claim 12,
wherein the primary cavity contains all the elements of the illumination circuit with the exception of the electrolytic switch;
wherein the LED of the illumination circuit is installed in the primary cavity such that the light generated by the LED will illuminated the electrolytic media;
wherein the electrolytic switch is installed in the switch cavity such that the electrolytic switch is immersed in the electrolytic media when the electrolytic media is drawn into the syringe.

14. The medical device according to claim 7
wherein the illumination circuit is an electrical circuit;
wherein the illumination circuit comprises a capacitor, a limit resistor, an electrolytic switch, and an LED;
wherein the capacitor, the limit resistor, the electrolytic switch, and the LED are electrically interconnected;
wherein the electrolytic switch comprises a second cathode and a second anode;
wherein the capacitor is further defined with a first cathode and a first anode;
wherein the LED is further defined with a third cathode and a third anode;
wherein the limit resistor is further defined with a first lead and a second lead.

15. The medical device according to claim 14
wherein the capacitor is an electrical charge storage device that powers the illumination circuit;
wherein the LED is a light source;
wherein the electrolytic switch is a switch that is actuated by the electrolytic media;
wherein the immersion of the electrolytic switch into the electrolytic media closes the electrolytic switch;
wherein the limit resistor is an electrical device that limits the current flow through the illumination circuit.

16. The medical device according to claim 15
wherein the first cathode of the capacitor is electrically connected to the first lead of the limit resistor;
wherein the second lead of the limit resistor is electrically connected to the second anode of the electrolytic switch;
wherein the second cathode of the electrolytic switch is electrically connected to the third anode of the LED;
wherein the third cathode of the LED is electrically connected to the first anode of the capacitor;
wherein the LED is selected such that the LED will illuminate the electrolytic media in a contrasting color;
wherein it is preferred that the color of the LED be a violet (440 nm to 480 nm) LED for this purpose.

17. The medical device according to claim 16 wherein the electrolytic media comprises a pharmacologically active media dissolved in a PBS solution.

18. The medical device according to claim 17
wherein the primary cavity contains all the elements of the illumination circuit with the exception of the electrolytic switch;
wherein the LED of the illumination circuit is installed in the primary cavity such that the light generated by the LED will illuminated the electrolytic media;
wherein the electrolytic switch is installed in the switch cavity such that the electrolytic switch is immersed in the electrolytic media when the electrolytic media is drawn into the syringe.

* * * * *